United States Patent
Kusama et al.

(10) Patent No.: US 8,158,772 B2
(45) Date of Patent: Apr. 17, 2012

(54) OLIGONUCLEOTIDE SEQUENCES THAT IDENTIFY SPECIES OF ANIMAL

(75) Inventors: Toyoko Kusama, Chiba (JP); Koichi Kadowaki, Ibaraki (JP); Tetsuya Nomura, Saitama (JP)

(73) Assignees: National Institute of Agrobiological Sciences, Ibaraki (JP); Incorporated Administrative Agency Fertilizer and Feed Inspection Services, Saitama (JP)

( * ) Notice: Subject to any disclaimer, the term of this patent is extended or adjusted under 35 U.S.C. 154(b) by 838 days.

(21) Appl. No.: 10/826,119

(22) Filed: Apr. 16, 2004

(65) Prior Publication Data

US 2005/0233334 A1    Oct. 20, 2005

(51) Int. Cl.
*C07H 21/04* (2006.01)
*C12Q 1/68* (2006.01)
(52) U.S. Cl. .................................... 536/24.33; 435/6.12
(58) Field of Classification Search ............. 435/6, 91.2, 435/6.12; 536/24.33
See application file for complete search history.

(56) References Cited

FOREIGN PATENT DOCUMENTS
JP      2003-164287     *  6/2003

OTHER PUBLICATIONS

Saulle et al., Rapid communication: Nucleotide sequence of Chamois, Alpine ibex, and Red deer tRNA Lys and ATPase8 mitochondrial genes. J Anim. Sci., vol. 77, pp. 3398-3399, 1999.*
Lowe et al., A computer program for selection of oligonucleotide primers for polymerase chain reactions. Nucleic Acids Research, vol. 18, No. 7, pp. 1757-1761, 1990.*
Chung Hy et al, Genbank Accession No. AY526085, Feb. 16, 2004.
Yang J et al, Genbank Accession No. AF486874, Jan. 20, 2004.
Hiendleder S et al, Genbank Accession No. AF010406, Dec. 13, 2000.
Feligini M et al, Genbank Accession No. AF533441, Jul. 23, 2003.
Inoue JG et al, Genbank Accession No. AB032554, Oct. 23, 2003.
Bland MM et al, Genbank Accession No. M18339, Jul. 21, 1995.
Lahiff, S., et al., Molecular and Cellular Probes, (2001) vol. 15, pp. 27-35, Ireland.
Tartaglia, M., et al., Journal of Food Protection, (1998) vol. 61, pp. 513-518, Italy.

* cited by examiner

*Primary Examiner* — Prabha Chunduru
(74) *Attorney, Agent, or Firm* — Turocy & Watson, LLP

(57) ABSTRACT

Methods for identifying animal species involving amplifying a DNA fragment by PCR using a DNA in a sample as a template and animal-specific DNA sequences as a primer pair, the animal-specific DNA sequences derived from a ATP synthase subunit 8 gene or a region proximal thereto of a mitochondrial genome; and detecting the amplified DNA fragment.

3 Claims, 18 Drawing Sheets

| | | |
|---|---|---|
| 1 | Cattle | ca-ta-tactctccttggtgac--atgccgcaactagacacgtcaacatgactgacaatgatcttatcaatattcttgacccttttatcatcttttcaactaaagtttcaaaacacaact |
| 2 | Chicken | ------------c---atgccccaattaaaccaaaccca-tgattctc[catcatactcctacttg]attcaccttctctcgttatccaacctaaactttcttcattcactc |
| 3 | Pig | ---ctaaatctccctcaat-ggta[tgccacaactagatacatct]ac[atgattcattacaattac]atcaataattataaacattatttattccaactaaaatctcaaactactcat |

| | | |
|---|---|---|
| 1 | Cattle | tttatcacaatcagaactgaccaacaacaaaatattaaaacaaacaaaacacccccttgagaaacaaaatgaacgaaaatttatttaccctctttattaccctgtaa--- |
| 2 | Chicken | taacaaacaacc--ctgcaaacaaaattaca-acaactaaacca-acaactaaaccc-acccc-c-tgaa[cctgaccatgaacctaa-]--------------- |
| 3 | Pig | accagcaa[gcccagaatcaattcaact]ca[aaactca]aaaaca]a[gcaccccttgagaataa]aatgaacgaaaatctattgcctctttattgccctacgataa |

Fig. 3

PCR Using Primer Pair for Detecting Ruminant-Specific DNA Sequence 104 bp

1 Cattle  2 Sheep  3 Goat  4 Deer  5 Pig  6 Horse
7 Rabbit  8 Whale  9 Chicken  10 Codfish  11 Salmon
12 Pilchard  13 Crab  14 Prawn  15 Clam  M Marker PCR Using Primer Pair (cow51 and cow3) for Detecting Cattle-Specific DNA Sequence 1 Cattle  2 Sheep  3 Goat
4 Pig    5 Chicken  M Marker PCR Using Pig-Specific Primer Pair 1 Cattle    2 Sheep    3 Goat
4 Pig      5 Chicken   M Marker PCR Using Pig-Specific Primer Pair ←126bp 1 Cattle   2 Sheep   3 Goat   4 Deer   5 Pig   6 Horse
7 Rabbit   8 Whale   9 Chicken   10 Codfish   11 Salmon
12 Pilchard   13 Crab   14 Prawn   15 Clam   M Marker PCR Using Chicken-Specific Primer Pair 1 Cattle  2 Sheep  3 Goat
4 Pig     5 Chicken  M Marker 1 Meat and Bonemeal
2 10% Meat and Bonemeal in Mixed Feed
3 1% Meat and Bonemeal in Mixed Feed
4 0.1% Meat and Bonemeal in Mixed Feed
5 0.01% Meat and Bonemeal in Mixed Feed
6 Mixed Feed
7 Negative Control (Without DNA Template)
M Marker Detection of DNA Sequence in Mixed Feed containing Meat and Bonemeal Using Ruminant-Specific Primer pair 1 Meat and Bonemeal
2 10% Meat and Bonemeal in Mixed Feed
3 1% Meat and Bonemeal in Mixed Feed
4 0.1% Meat and Bonemeal in Mixed Feed
5 0.01% Meat and Bonemeal in Mixed Feed
6 0.001% Meat and Bonemeal in Mixed Feed
7 0.0001% Meat and Bonemeal in Mixed Feed
8 Mixed Feed
M Marker Detection of DNA Sequence in Mixed Feed containing Meat and Bonemeal Using Cattle-Specific Primer pair 1 Meat and Bonemeal
2 10% Meat and Bonemeal in Mixed Feed
3 1% Meat and Bonemeal in Mixed Feed
4 0.1% Meat and Bonemeal in Mixed Feed
5 0.01% Meat and Bonemeal in Mixed Feed
6 0.001% Meat and Bonemeal in Mixed Feed
7 0.0001% Meat and Bonemeal in Mixed Feed
8 Mixed Feed
M Marker

SEQUENCE LISTING

<160> NUMBER OF SEQ ID NOS: 43

<210> SEQ ID NO 1
<211> LENGTH: 20
<212> TYPE: DNA
<213> ORGANISM: Artificial Sequence
<220> FEATURE:

<223> OTHER INFORMATION: primer

<400> SEQUENCE: 1
aactagacac gtcaacatga                                          20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
aggtaaataa attttcgttc                                          20

<210> SEQ ID NO 3
<211> LENGTH: 18
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.
<220> FEATURE:
<221> NAME/KEY: misc_feature
<223> OTHER INFORMATION: k is g or t.

<400> SEQUENCE: 3
acrtcaacrt gactkaca                                            18

<210> SEQ ID NO 4
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.

<400> SEQUENCE: 4
tctggrttgt grtaraagt                                           19

<210> SEQ ID NO 5
<211> LENGTH: 21
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.
<220> FEATURE:
<221> NAME/KEY: misc_feature
<223> OTHER INFORMATION: k is g or t.

<400> SEQUENCE: 5
gacacrtcaa crtgactkac a                                        21

<210> SEQ ID NO 6
<211> LENGTH: 22
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.

<400> SEQUENCE: 6
arttctggrt tgtgrtaraa gt                                    22

<210> SEQ ID NO 7
<211> LENGTH: 19
<212> TYPE: DNA
<213> ORGANISM: Artificial Sequence
<220> FEATURE:
<223> OTHER INFORMATION: primer

<400> SEQUENCE: 7
gtcaacatga ctgacaatg                                        19

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
agacacgtca acatgactg                                        19

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
atgatcttat caatattctt g                                     21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
gacatgccgc aactagacac g                                     21

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
ctctccttgg tgacatgccg                                       20

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
ttttaatatt tttgttggtg tc                                    22

<210> SEQ ID NO 13
<211> LENGTH: 21
<212> TYPE: DNA

```
<213> ORGANISM: Artificial Sequence
<220> FEATURE:
<223> OTHER INFORMATION: primer

<400> SEQUENCE: 13 tcaagggtg ttttgtttta a                                          21

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
acaatgatct tatcaatatt cttg                                      24

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
ccttcaaggg gtgttttgtt ttaa                                      24

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
atgattcatt acaattac                                             18

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tgccacaact agatacatct                                           20

<210> SEQ ID NO 18
<211> LENGTH: 24
<212> TYPE: DNA
<213> ORGANISM: Artificial Sequence
<220> FEATURE:
<223> OTHER INFORMATION: primer

<400> SEQUENCE: 18
atctacatga ttcattacaa ttac                                      24

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
ttatttctca agggtgc                                              18
```

<210> SEQ ID NO 20
<211> LENGTH: 21
<212> TYPE: DNA
<213> ORGANISM: Artificial Sequence
<220> FEATURE:
<223> OTHER INFORMATION: primer

<400> SEQUENCE: 20
tgagttcaat tgattctggg c                                                  21

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tgtttttgag ttttgagttc a                                                  21

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
ctatgttttt gagttttgag ttca                                               24

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
aattctatca atatttttag t                                                  21

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctcaaggagt attttgtttc                                                    20

<210> SEQ ID NO 25
<211> LENGTH: 19
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.

<400> SEQUENCE: 25
gccacaacta gacacatcr                                                     19

<210> SEQ ID NO 26
<211> LENGTH: 18
<212> TYPE: DNA
<213> ORGANISM: Artificial Sequence

```
<220> FEATURE:
<223> OTHER INFORMATION: primer

<400> SEQUENCE: 26
tctcaagggg tgttatgc                                                      18

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
ttctgggttg tggtagaagt c                                                  21

<210> SEQ ID NO 28
<211> LENGTH: 18
<212> TYPE: DNA
<213> ORGANISM: Artificial Sequence
<220> FEATURE:
<223> OTHER INFORMATION: primer

<400> SEQUENCE: 28
catcatactc ctaacttg                                                      18

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
cctaacttga ttcaccttct c                                                  21

<210> SEQ ID NO 30
<211> LENGTH: 18
<212> TYPE: DNA
<213> ORGANISM: Artificial Sequence
<220> FEATURE:
<223> OTHER INFORMATION: primer

<400> SEQUENCE: 30
tttaggttca tggtcagg                                                      18

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
gttcatggtc aggttcaggg g                                                  21

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
atcctcactc atacttgaag                                                    20
```

```
<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
actggtcaaa gaagcttagt                                              20

<210> SEQ ID NO 34
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: w is a or t.
<220> FEATURE:
<221> NAME/KEY: misc_feature
<223> OTHER INFORMATION: m is a or c.

<400> SEQUENCE: 34
atcctcwctm atamttgaag                                              20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
agtatcatgg tcaggttcag                                              20

<210> SEQ ID NO 36
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: r is a or g.
<220> FEATURE:
<221> NAME/KEY: misc_feature
<223> OTHER INFORMATION: k is g or t.

<400> SEQUENCE: 36
agtrtcatgg tcagkttcag                                              20

<210> SEQ ID NO 37
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<223> OTHER INFORMATION: y is c or t.
<220> FEATURE:
<221> NAME/KEY: misc_feature
<223> OTHER INFORMATION: r is a or g.

<400> SEQUENCE: 37
aytgrtcaaa gargcttagt                                              20

<210> SEQ ID NO 38
<211> LENGTH: 20
```

```
<212> TYPE: DNA
<213> ORGANISM: Artificial Sequence
<220> FEATURE:
<223> OTHER INFORMATION: primer

<400> SEQUENCE: 38
atgcctcaat taaaccccgc                                               20

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
gcccacaact tcaacaacga                                               20

<210> SEQ ID NO 40
<211> LENGTH: 20
<212> TYPE: DNA
<213> ORGANISM: Artificial Sequence
<220> FEATURE:
<223> OTHER INFORMATION: primer

<400> SEQUENCE: 40 gcccccctggt ttgcaattct                                              20

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
acctctagtg acatgcctca                                               20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
atgttagaag gagctaaatc                                               20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
ccgaatgatt gtttagccaa                                               20
```

OLIGONUCLEOTIDE SEQUENCES THAT IDENTIFY SPECIES OF ANIMAL

BACKGROUND OF THE INVENTION

1. Field of the Invention

The present invention relates to methods for identifying animal species and animal-derived DNA-specific primer pairs used therein. More specifically, the present invention relates to methods for identifying animal species that include a step of amplifying an animal-specific DNA sequence derived from the ATP synthase subunit 8 gene of a mitochondrial genome, and primer pairs used in this amplification step.

2. Description of the Related Art

Currently, there is a problem that cattle is infected with bovine spongiform encephalopathy (BSE) by giving feed containing meat and bonemeal derived from cattle infected with BSE. It has been shown that BSE-like diseases may be present in various livestock as well. Accordingly, since the emergence of BSE, there has been a need to develop sensitive and effective method to identify feed contaminated bone and bonemeal, and this has become a particularly urgent matter for authorities.

Immunological methods and gene identification methods using nuclear gene conventionally have been used as methods for identifying animal species. Examples of immunological methods include ELISA and immunoblotting. PCR is an example of a gene identification method using nuclear gene. However, there are many problems with methods for identifying the animal species that are currently employed. For example, in meat and bonemeal that has been heat-treated, there is a high likelihood that nucleic acids have been fragmented. Furthermore, majority of feed in which meat and bonemeal has been mixed is composed of plant-derived material. Therefore, it is necessary to analyze trace amounts of animal-derived components. There is a dire need for the development of a detection method that is highly sensitive and effective and that can be executed with respect to such heat-treated samples.

Accordingly, a method other than immunological methods and gene identification methods employing nuclear gene that is for detecting and identifying the animal species of animal-derived components that are present in trace amounts is desirable. In particular, it is crucial to identify the type of animal meat, meat and bonemeal, or fishmeal used in feed given to livestock and pets. Furthermore, it is desirable that the detection method is highly sensitive and differentiate species of animal DNA present in trace amounts from among large quantities of plant DNA or DNA of other animal species.

SUMMARY OF THE INVENTION

The inventors of the present application focused on the mitochondrial genome, which is inherited maternally and exists in a greater number of copies than nuclear genome, and investigated the use of mitochondrial gene as a target for identifying animal species. Their research indicated that the homologous sequence with ATP synthase subunit 8 gene (atp8 gene) from animal mitochondrial genome is not present in plant (*Oryza sativa*) mitochondrial genome. Thus, the inventors found that the DNA derived from the atp8 gene can serve as a material for specific detection of trace amounts of animal DNA among plant-based feed, in other word, plant atp8 gene is very diverged from animal atp8 gene, and also that specific DNA sequences of the animal mitochondrial atp8 gene can be used to identify the animal species, thereby arriving at the present invention.

The present invention provides a method for identifying animal species, said method comprises:
amplifying a DNA sequence by PCR using a DNA in a sample as a template and animal-specific DNA sequences as a primer pair, wherein the animal-specific DNA sequences are derived from a ATP synthase subunit 8 gene or a region proximal thereto of a mitochondrial genome, and
detecting the amplified DNA sequence.

In a preferred embodiment, the animal is a mammal, and further preferably, the primer pair is a combination of the DNA sequence of SEQ ID NO: 1 and the DNA sequence of SEQ ID NO: 2.

In a further preferred embodiment, the mammal is selected from the group consisting of cattle, sheep, goat, deer, pig, horse, rabbit, and whale.

In a preferred embodiment, the animal is a ruminant, and further preferably, the primer pair is a combination of the DNA sequence of SEQ ID NO: 3 and the DNA sequence of SEQ ID NO: 4, or a combination of the DNA sequence of SEQ ID NO: 5 and the DNA sequence of SEQ ID NO: 6.

In a further preferred embodiment, the ruminant is selected from the group consisting of cattle, sheep, goat, and deer.

In a preferred embodiment, the animal is a cattle, and further preferably, the primer pair is a combination of DNA sequences selected from the group consisting of the following DNA sequence combinations: SEQ ID NO: 9 and SEQ ID NO: 13; SEQ ID NO: 9 and SEQ ID NO: 12; SEQ ID NO: 11 and SEQ ID NO: 13; SEQ ID NO: 10 and SEQ ID NO: 12; SEQ ID NO: 11 and SEQ ID NO: 12; SEQ ID NO: 8 and SEQ ID NO: 12; and SEQ ID NO: 14 and SEQ ID NO: 15.

In a preferred embodiment, the animal is a pig, and further preferably, the primer pair is a combination of the DNA sequence of SEQ ID NO: 17 and the DNA sequence of SEQ ID NO: 19, or a combination of the DNA sequence of SEQ ID NO: 18 and the DNA sequence of SEQ ID NO: 22.

In a preferred embodiment, the animal is a sheep, and further preferably, the primer pair is a combination of the DNA sequence of SEQ ID NO: 23 and the DNA sequence of SEQ ID NO: 24.

In a preferred embodiment, the animal is a goat, and further preferably, the primer pair is a combination of the DNA sequence of SEQ ID NO: 25 and the DNA sequence of SEQ ID NO: 26.

In a preferred embodiment, the animal is a chicken, and further preferably, the primer pair is a combination of the DNA sequence of SEQ ID NO: 28 and the DNA sequence of SEQ ID NO: 30.

In a preferred embodiment, the animal is a fish, and further preferably, the primer pair is a combination of the DNA sequence selected from the group consisting of SEQ ID NOS: 32, 34, 38 and 39 and the DNA sequence selected from the group consisting of SEQ ID NOS: 33, 35, 36, 37, 40, and 41.

In a further preferred embodiment, the fish is selected from the group consisting of sardine, flatfish, salmon, Alaska Pollack, tuna, and lady crab.

In a further preferred embodiment, the sample is selected from a group consisting of raw meat, raw fish, processed meat food products, processed fish food products, food products containing processed meat, food products containing processed fish, blood, hair, body fluids, milk, milk processing products, meat and bonemeal, bonemeal, fishmeal, fish soluble, and feed, fertilizer, and feed additive containing them.

The present invention also provides a primer pair for detection of a mammal-specific DNA, the primer pair being a combination of the DNA sequence of SEQ ID NO: 1 and the DNA sequence of SEQ ID NO: 2.

In a preferred embodiment, the mammal is selected from the group consisting of cattle, sheep, goat, deer, pig, horse, rabbit, and whale.

The present invention also provides a primer pair for detection of a ruminant-specific DNA, the primer pair being a combination of the DNA sequence of SEQ ID NO: 3 and the DNA sequence of SEQ ID NO: 4, or a combination of the DNA sequence of SEQ ID NO: 5 and the DNA sequence of SEQ ID NO: 6.

In a preferred embodiment, the ruminant is selected from the group consisting of cattle, sheep, goat, and deer.

The present invention also provides a primer pair for detection of a cattle-specific DNA, the primer pair being a combination of DNA sequences selected from the group consisting of the following DNA sequence combinations: SEQ ID NO: 9 and SEQ ID NO: 13; SEQ ID NO: 9 and SEQ ID NO: 12; SEQ ID NO: 11 and SEQ ID NO: 13; SEQ ID NO: 10 and SEQ ID NO: 12; SEQ ID NO: 11 and SEQ ID NO: 12; SEQ ID NO: 8 and SEQ ID NO: 12; and SEQ ID NO: 14 and SEQ ID NO: 15.

The present invention also provides a primer pair for detection of a pig-specific DNA, the primer pair being a combination of the DNA sequence of SEQ ID NO: 17 and the DNA sequence of SEQ ID NO: 19, or a combination the DNA sequence of SEQ ID NO: 18 and the DNA sequence of SEQ ID NO: 22.

The present invention also provides a primer pair for detection of a sheep-specific DNA, the primer pair being a combination of the DNA sequence of SEQ ID NO: 23 and the DNA sequence of SEQ ID NO: 24.

The present invention also provides a primer pair for detection of a goat-specific DNA, the primer pair being a combination of the DNA sequence of SEQ ID NO: 25 and the DNA sequence of SEQ ID NO: 26.

The present invention also provides a primer pair for detection of a chicken-specific DNA, the primer pair being a combination of the DNA sequence of SEQ ID NO: 28 and the DNA sequence of SEQ ID NO: 30.

The present invention also provides a primer pair for detection of a fish-specific DNA, the primer pair being a combination of the DNA sequence selected from the group consisting of SEQ ID NOS: 32, 34, 38 and 39 and the DNA sequence selected from the group consisting of SEQ ID NOS: 33, 35, 36, 37, 40, and 41.

In a preferred embodiment, the fish is selected from the group consisting of sardine, flatfish, salmon, Alaska Pollack, tuna, and lady crab.

The present invention also provides a primer pair for detection of a plant-specific DNA, the primer pair being a combination of the DNA sequence of SEQ ID NO: 42 and the DNA sequence of SEQ ID NO: 43.

Further, the present invention provides a method for detecting animal-derived components present in mixed feed, said method comprises:
amplifying a DNA sequence by PCR using a DNA in a sample as a template and animal-specific DNA sequences as a primer pair, wherein the animal-specific DNA sequences are derived from a ATP synthase subunit 8 gene or a region proximal thereto of a mitochondrial genome, and
detecting the amplified DNA sequence.

The present invention also provides a kit for detecting an animal-derived component present in a sample, said kit comprises at least one of primer pair specific for any animal described above.

In a preferred embodiment, the kit further comprises a primer pair for detection of a plant-specific DNA, said primer pair is a combination of the DNA sequence of SEQ ID NO: 42 and the DNA sequence of SEQ ID NO: 43.

Further, the present invention provides a method for detecting plant-derived components present in sample, said method comprises:
amplifying a DNA sequence by PCR using a DNA in a sample as a template and plant-specific DNA sequences as a primer pair, wherein the plant-specific DNA sequences are derived from a ATP synthase subunit 8 gene or a region proximal thereto of a mitochondrial genome, and
detecting the amplified DNA sequence.

Using the method of the present invention, it is possible to detect, with high sensitivity, trace amounts of animal-derived DNA in a sample. It is thus applicable to identify the animal species of trace amounts of meat and bonemeal mixed into feed. More particularly, detection is possible even if trace amounts of cattle-derived meat and bonemeal are mixed into mixed feed for livestock. Further, the primers for the detection of fish-specific DNA according to the present invention are useful for detecting a wide range of fishmeal derived from various fish species that has been mixed into mixed feed or the like.

BRIEF DESCRIPTION OF DRAWINGS

FIG. 1 shows a sequence alignment of mitochondrial atp8 genes derived from various types of animals.

FIG. 2 shows a sequence alignment of chicken, cattle, and pig mitochondrial atp8 genes.

FIG. 3 shows a sequence alignment of mitochondrial atp8 genes, and nearby regions, derived from various types of animals.

DESCRIPTION OF THE PREFERRED EMBODIMENT

Figure 4:
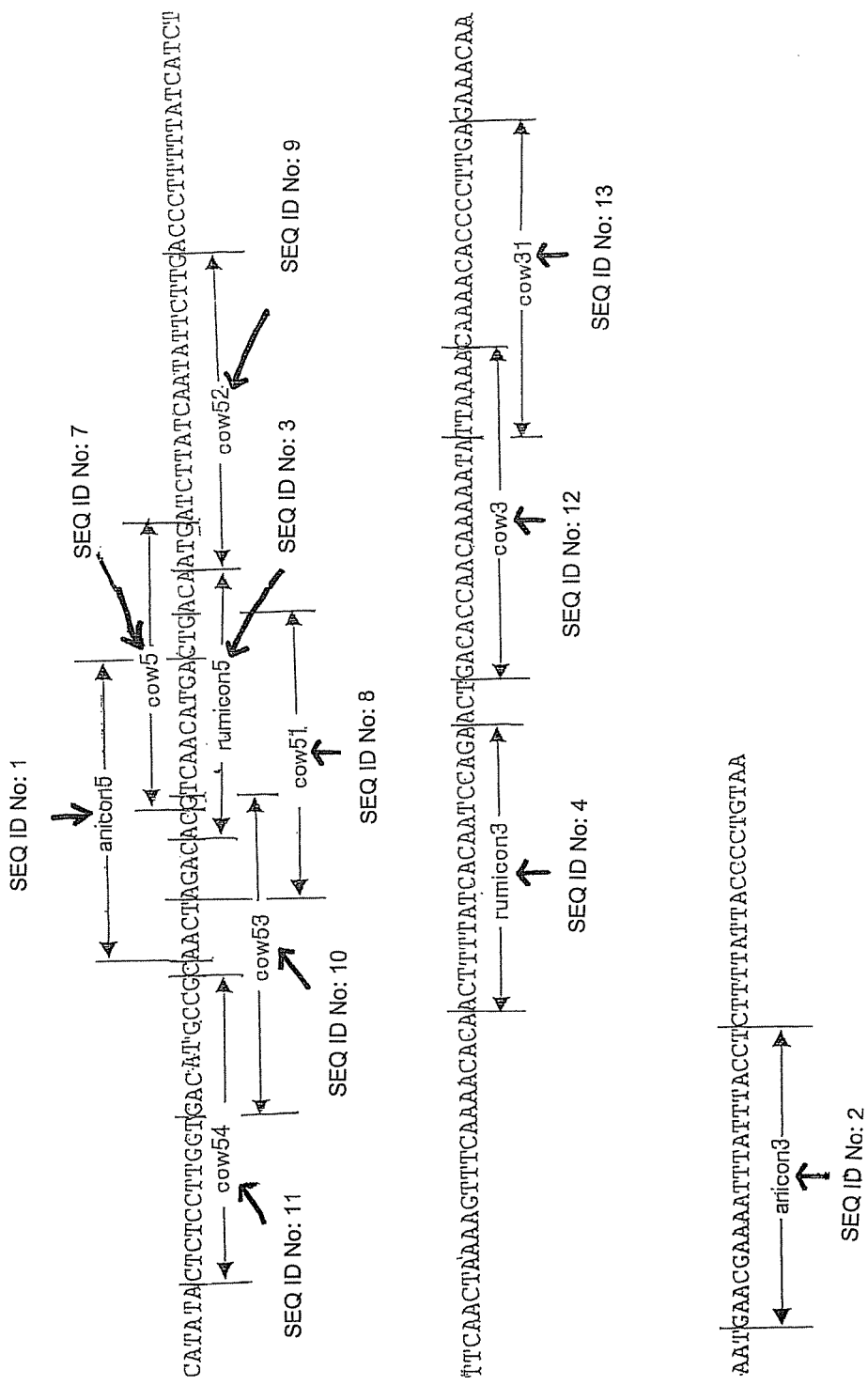
FIG. 4 shows the positional relationship on the mitochondrial atp8 gene of the primers used to specifically detect cattle-derived DNA sequences.

The mitochondrial genome is essential for the biosynthesis of the enzymes required for oxidative phosphorylation (electron transport system), and mitochondrial DNA codes for ATP synthase and cytochrome c oxidase, and the like. ATP synthase is composed of several subunits, and as discussed above, the inventors found that the ATP synthase subunit 8 gene (atp8 gene) is present in the animal mitochondrial genome but homologous sequence with animal atp8 gene is not present in the plant (Oryza sativa) mitochondrial genome. It thus became possible to identify animal species even when plant-derived DNA is present in large quantities in the feed.

Figure 1:
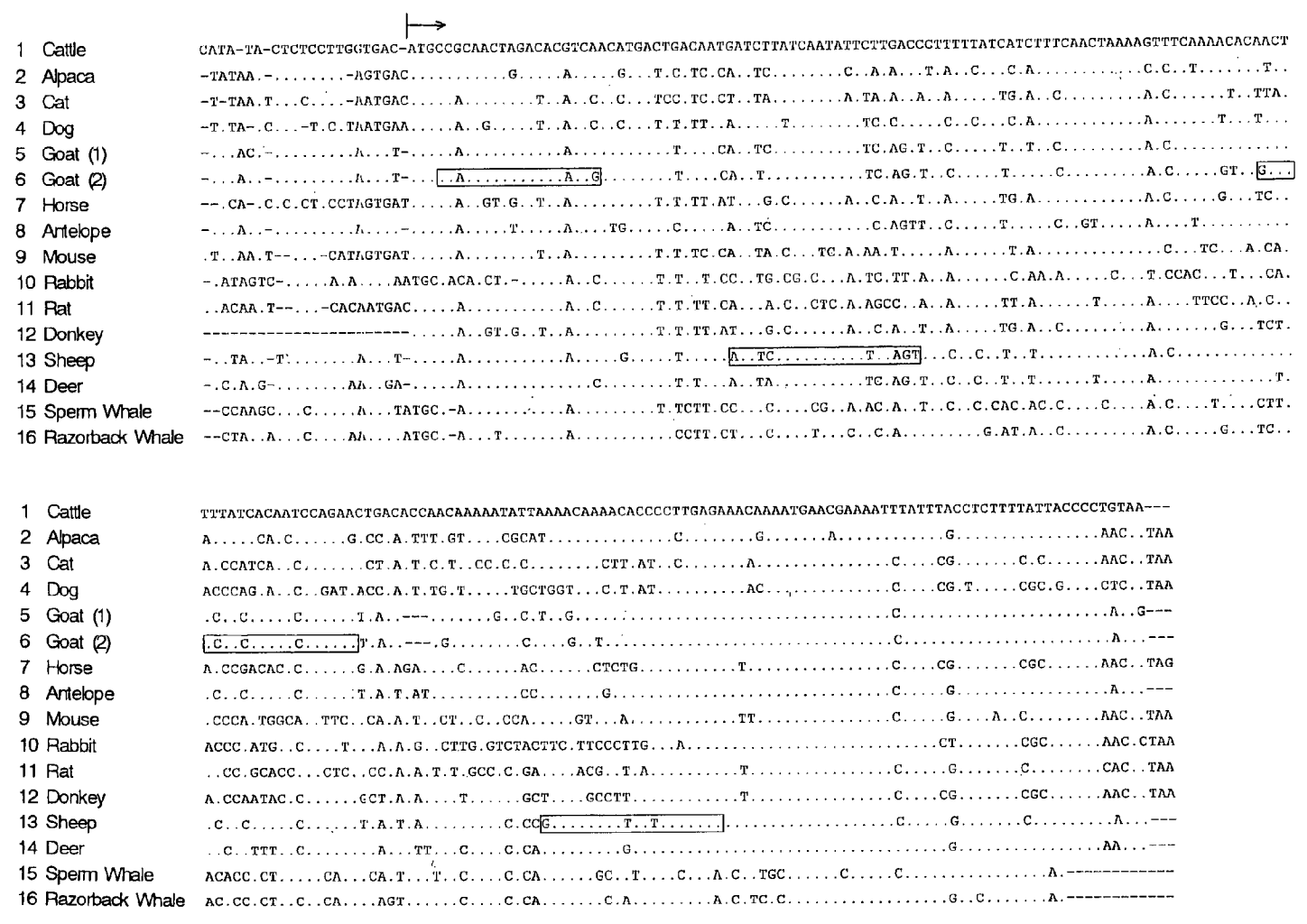

Several animal atp8 genes are known. For example, taking the cattle atp8 DNA sequence (cattle) as a reference, the atp8 DNA sequences of several animal species were aligned so that homology with the cow sequence is achieved, and this is shown in FIG. 1. FIG. 1 shows the DNA sequence of the atp8 gene of 1: cattle, 2: alpaca, 3: cat, 4: dog, 5: goat (1), 6: goat (2), 7: horse, 8: antelope, 9: mouse, 10: rabbit, 11: rat, 12: donkey, 13: sheep, 14: deer, 15: sperm whale, and 16: razorback whale. It should be noted that the arrow in the diagram indicates the start position of the cattle atp8 reading frame.

FIG. 2 shows the atp8 genes of cattle, chicken, and pig aligned with one another. Further, FIG. 3 shows the atp8 genes of fish, chicken, cattle, sheep, and pig aligned with one another, and the underlined portion indicates the position of the atp8 gene of a pilchard.

As shown in FIGS. 1 to 3, there is diversity of DNA sequences among the atp8 genes. This diversity can be used to detect specific sequences in various types of animals, thereby allowing various animal species to be identified.

To identify various types of animals, examples of methods for detecting a DNA sequence specific to an animal species include Southern Blotting and PCR (polymerase chain reaction). PCR is preferably used in the present invention because it permits detection even with very small DNA samples and it allows accuracy to be improved. In the present invention, PCR is carried out using a pair of primers including a DNA sequence specific to a target animal species, and a DNA fragment that is amplified is detected.

PCR is for example carried out as follows. First, two regions are selected as primers from any of regions of the atp8 gene and regions proximal thereto having a DNA sequence specific to a target animal species, and the selected primers are synthesized. Using this pair of primers, the DNA fragment of the region sandwiched between the two primers is amplified by PCR. A sample containing the amplified DNA fragments is then subjected to electrophoresis to determine whether that DNA fragment is present.

A primer is a DNA sequence of nucleotides in any length, and is suitably selected based on the sequence alignment of the atp8 genes of various types of animals in publicly available databases. For example, in order to detect DNA specific to mammals, a region having higher homology with mammals and low homology with non-mammals and having appropriate nucleotide at the 3' end can be chosen. In order to detect DNA specific to a certain animal, a region having specificity to that animal and low specificity with other animals can be chosen. Since primers are used in pairs, two regions, that is, a region on the 5' side and a region on the 3' side, are selected. If more than two regions can be selected as primers, then it is possible to use various primer combinations.

For example, FIG. 4 shows a DNA sequence of cattle mitochondrial atp8 gene, and the markings in the diagram are the regions (sequences) that can be used as primers for detecting cattle-specific DNA. DNA sequences for specifically detecting mammals (anicon5 [SEQ ID NO: 1] and anicon3 [SEQ ID NO: 2]) and DNA sequences for specifically detecting ruminants (rumicon5 [SEQ ID NO: 3] and rumicon3 [SEQ ID NO: 4]) are also shown in FIG. 4. A more detailed explanation follows in the Examples. For example, mammal specific DNA can be detected when anicon5 is used as the 5' primer and anicon3 is used as the 3' primer. Likewise, ruminant specific DNA can be detected when rumicon5 and rumicon3 are used as primers. Alternatively, although not shown, it is also possible to combine Fpr-F [SEQ ID NO: 5] and Fpr-R [SEQ ID NO: 6] to detect ruminant specific DNA with greater accuracy. As the 5' primer, any one of cow5 [SEQ ID NO: 7], cow51 [SEQ ID NO: 8], cow52 [SEQ ID NO: 9], cow53 [SEQ ID NO: 10], and cow54 [SEQ ID NO: 11] is used, and as the 3' primer, either cow3 [SEQ ID NO: 12] or cow31 [SEQ ID NO: 13] is used. For example, the primer pairs of cow52 and cow31, cow52 and cow3, cow54 and cow31, cow53 and cow3, cow54 and cow3, and cow51 and cow3 are capable of detecting cattle-specific DNA. Alternatively, although not shown, it is also possible to combine Fpc-F [SEQ ID NO: 14] and Fpc-R [SEQ ID NO: 15] to detect cattle-specific DNA with greater accuracy.

The regions surrounded by squares in FIGS. 1 to 3 indicate examples of DNA sequences used in tests for specifically detecting DNAs derived from the respective animal species.

The DNA sequences of the regions selected as primers are synthesized by normally employed methods. Typically, nucleotides are extended on a support medium using an automated DNA synthesizer, then removed from protecting group and cleaved from the support medium. Then, they can be purified using a normally employed method (such as column chromatography) to obtain primers of interest.

Samples that can be measured include raw meat, raw fish, processed meat food products, processed fish food products, food products containing processed meat, food products containing processed fish, blood, hair, body fluids, milk, milk processing products, meat and bonemeal, bonemeal, fishmeal, fish soluble, and feed, fertilizer, and feed additive containing them. Extraction of mitochondrial DNA from these samples is, for example, performed as follows. Approximately 50 mg to 500 mg of a sample (for example, 50 mg in the case of raw meat, 100 mg to 500 mg in the case of a dried powder sample) is suspended in about 10 times that amount of buffered solution, ground using a bead grinding method, for example, and then extracted using a commercially available tissue cell mitochondrial DNA extraction kit (manufactured by Wako Pure Chemical Industries, Ltd., for example). Such kits allow purer mitochondrial DNA to be collected in that little genome DNA in the tissue cells is contaminated. For example, to the sample ground is added a reagent in the kit, and centrifuged, and the pellets are collected to concentrate. It is thus possible to more efficiently extract mitochondrial DNA with little contamination of genome DNA, which is present in large quantities in the sample. The method for extracting DNA is not limited to those described herein, and it is apparent to those skilled in the art to employ other methods for extracting DNA.

There are no particular limitations regarding the amount of primer used, but generally is it preferable that approximately 0.4 µM is used.

PCR is performed on the pretreated sample, that is, either the mitochondrial DNA or total DNA extracted from the sample, using the primer pair selected above, so as to amplify the DNA fragment of the region sandwiched between the primers. PCR is executed under conditions in which it is ordinarily performed, and conditions that are appropriate for each primer pair are set. For example, DNA fragment is, firstly, heat denatured at 95° C. for 9 minutes; then subjected to the cycle of reactions of denaturing at 92° C. for 30 seconds to one minute, annealing at 40 to 65° C. for 30 seconds to two minutes, and extending at 72° C. for 30 seconds to two minutes, which is repeated 30 to 50 times; and finally, allowed to react at 72° C. for five minutes to finish PCR. AmpliTaq GOLD polymerase or the like is used as the DNA polymerase. The size of the PCR product (DNA fragment) amplified by the primer pair can be approximately 100 bp to approximately 300 bp, although this varies depending on the number of bases between the primer pair that has been selected. The PCR product is then subjected to agarose or polyacrylamide gel electrophoresis, for example, under conditions in which the above DNA fragments can be separated.

The DNA fragments on the gel subjected to electrophoresis can be detected by detection means normally employed by those skilled in the art, such as ethidium bromide staining, silver staining, fluorescence detection, and Southern hybridization, and can be confirmed by DNA sequencing.

Thus, if mitochondrial DNA derived from a species of interest is present in the sample, then, amplified DNA fragments can be detected on the gel. Limits to detection may vary depending on various factors, such as the type and combination of the primer pair used, the amount of sample, the PCR conditions, and the detection method. If appropriate conditions are selected, then the presence of DNA can be detected with high sensitivity even in trace samples. For example, if appropriate conditions are selected when the sample is a mixed feed that contains cattle-derived meat and bonemeal, then contamination of only 0.001 wt % cattle meat and bonemeal in the feed can be detected using a specific cattle-specific primer pair.

It should be noted that when a sample is a mixed feed, if a plant DNA-specific primer pair (for example, the combination of placon5 [SEQ ID NO: 42] and placon3 [SEQ ID NO: 43]) is used as a control experiment, then it is possible to confirm whether or not DNA has been appropriately extracted from the sample. Furthermore, by using a plant DNA-specific primer pair, a plant-derived component present in a sample can be detected.

The primer pairs of the present invention may be provided in the form of a kit for detecting an animal-derived component present in a sample. The kit comprises at least one of primer pair specific for any animal described above. Preferably, the kit further comprises the plant DNA-specific primer pair as a control.

It should be noted that the primer sequence has been specified in the Examples discussed below, but there is no intention to limit the present invention to the following Examples. It is intended that the present invention includes in its scope sequences that include those primer sequences, or those sequences with one or more base sequence substitutions, deletions, or insertions or addition of nucleotide sequences to the 5' end, and sequences which by changing the hybridizing conditions can hybridize with a DNA of interest and allow a DNA derived from a specific animal species to be detected specifically.

EXAMPLES

Primer Synthesis

Primer regions to be used in the following Examples were selected based on the sequence alignment of the atp8 gene and regions proximal thereto of various animals shown in FIGS. 1 to 3. The DNA sequences of the selected regions were synthesized using an automated DNA synthesizer.

Example 1

Specific Detection of Mammal-Derived DNA Sequence

DNAs from 15 types of meat samples, these being cattle, sheep, goat, deer, pig, horse, rabbit, whale, chicken, codfish, salmon, sardine, crab, prawn, and clam, were prepared as follows. Each DNA sample was diluted in an appropriate concentration in buffer solution (10 mM Tris-HCl, pH 7.5, 20 mM EDTA, pH 7.5), ground using a bead grinding method, and then DNA was extracted using the mtDNA Extractor CT Kit (manufactured by Wako Pure Chemical Industries, Ltd.), which is a commercially available tissue cell mitochondrial DNA extraction kit.

Figure 5:
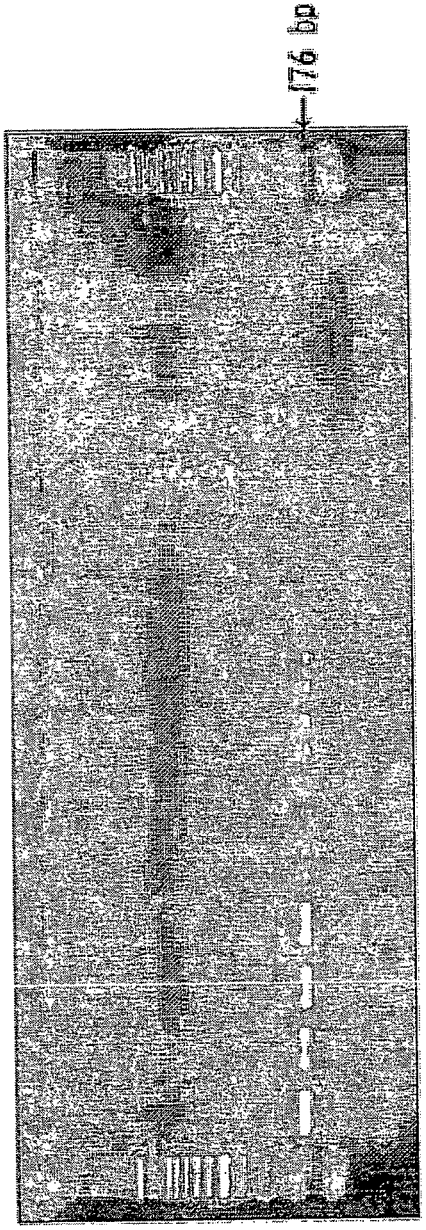
FIG. 5 is a photograph showing the results of electrophoresis after performing PCR using a primer pair (anicon5 and anicon3) for detecting mammal-specific DNA sequences and with DNAs derived from various types of animals serving as templates.

With each of these DNA samples serving as a template, PCR was performed using anicon5 [SEQ ID NO: 1] and anicon3 [SEQ ID NO: 2] as the 5' primer and the 3' primer, respectively. The PCR conditions were as follows: reaction buffer solution (10 mM Tris-HCl, pH 8.3, 50 mM KCl, 1.5 mM $MgCl_2$, 0.001% (w/v) gelatin); heat denaturing at 95° C. for 9 minutes, followed by the cycle of reactions of denaturing at 92° C. for one minute, annealing at 55° C. for two minutes, and extending for two minutes at 72° C. repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. The results are shown in FIG. 5. In the diagram, M is the molecular weight marker.

As is clear from FIG. 5, by performing PCR using anicon5 [SEQ ID NO: 1] and anicon3 [SEQ ID NO: 2] as primers with each animal-derived DNA serving as a template, the PCR products (amplified DNA fragments) were observed only in mammals (176 bp band position) (lanes 1 to 8). That is, it was demonstrated that by using anicon5 [SEQ ID NO: 1] and anicon3 [SEQ ID NO: 2] as the primer pair, it is possible to specifically detect only mammal-derived DNA from among various types of animal meat samples. Consequently, the combination of anicon5 [SEQ ID NO: 1] and anicon3 [SEQ ID NO: 2] is a primer pair that specifically detects the DNA sequence derived from animal species of mammalian origin. The regions that can be used as primers for detecting DNAs derived from mammals are shown in FIG. 4. It should be noted that this primer pair was designed so as to fail to amplify human DNA.

Example 2

Specific Detection of Ruminant-Derived DNA Sequence-1

With the 15 types of DNA samples prepared in the same manner as in Example 1 (except that a different type of cattle DNA sample was used in place of deer) serving as templates, PCR was performed using rumicon5 [SEQ ID NO: 3] and rumicon3 [SEQ ID NO: 4] as the 5' primer and the 3' primer, respectively. The PCR conditions were as follows: heat denaturing at 95° C. for 9 minutes, followed by the cycle of reactions of denaturing at 92° C. for one minute, annealing at 45° C. for two minutes, and extending at 72° C. for two minutes repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. The results are shown in FIG. 6.

Figure 6:
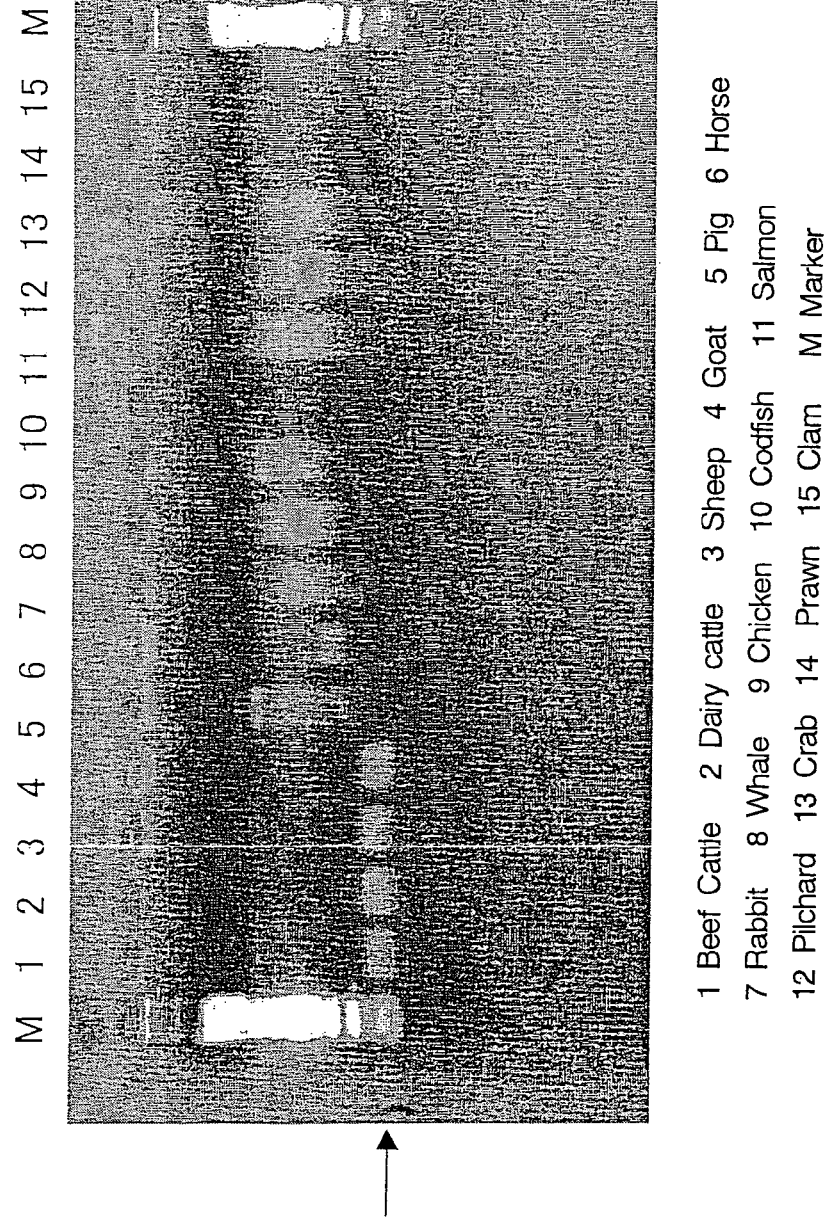
FIG. 6 is a photograph showing the results of electrophoresis after performing PCR using a primer pair (rumicon5 and rumicon3) for detecting ruminant-specific DNA sequences and with DNAs derived from various types of animals serving as templates.

As shown in FIG. 6, by performing PCR using rumicon5 [SEQ ID NO: 3] and rumicon3 [SEQ ID NO: 4] as primers with each animal-derived DNA serving as a template, PCR products from DNAs derived from beef cattle, dairy cattle, sheep, and goat, which are ruminants, were observed (band position indicated by the arrow). On the other hand, PCR products (DNA fragments) could not be detected in the DNA samples of animals that were not ruminants. That is, it was demonstrated that by using rumicon5 [SEQ ID NO: 3] and rumicon3 [SEQ ID NO: 4] as the primer pair, it is possible to specifically detect only ruminant-derived DNA from various types of animal meat samples. Consequently, the combination of rumicon5 [SEQ ID NO: 3] and rumicon3 [SEQ ID NO: 4] is a primer pair that specifically detects the DNA sequence derived from animal species of ruminant origin. The regions that can be used as the primers for detecting DNAs derived from ruminants are shown in FIG. 4.

It should be noted that in rumicon5 [SEQ ID NO: 3], "r" is "g" or "a" and "k" is "g" or "t". That is, rumicon5 [SEQ ID NO: 3] is a primer mixture, but it should be apparent to those skilled in the art that each can be used independently.

Example 3

Specific Detection of Ruminant-Derived DNA Sequence-2

With the 15 types of DNA samples prepared in the same manner as in Example 1 serving as templates, PCR was performed using Fpr-F [SEQ ID NO: 5] and Fpr-R [SEQ ID NO: 6] as the 5' primer and the 3' primer, respectively. The PCR conditions were as follows: heat denaturing at 95° C. for 9 minutes, followed by the cycle of reactions of denaturing at 92° C. for 30 seconds, annealing at 50° C. for 30 seconds, and extending at 72° C. for 30 seconds repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. The results are shown in FIG. 7.

Figure 7:
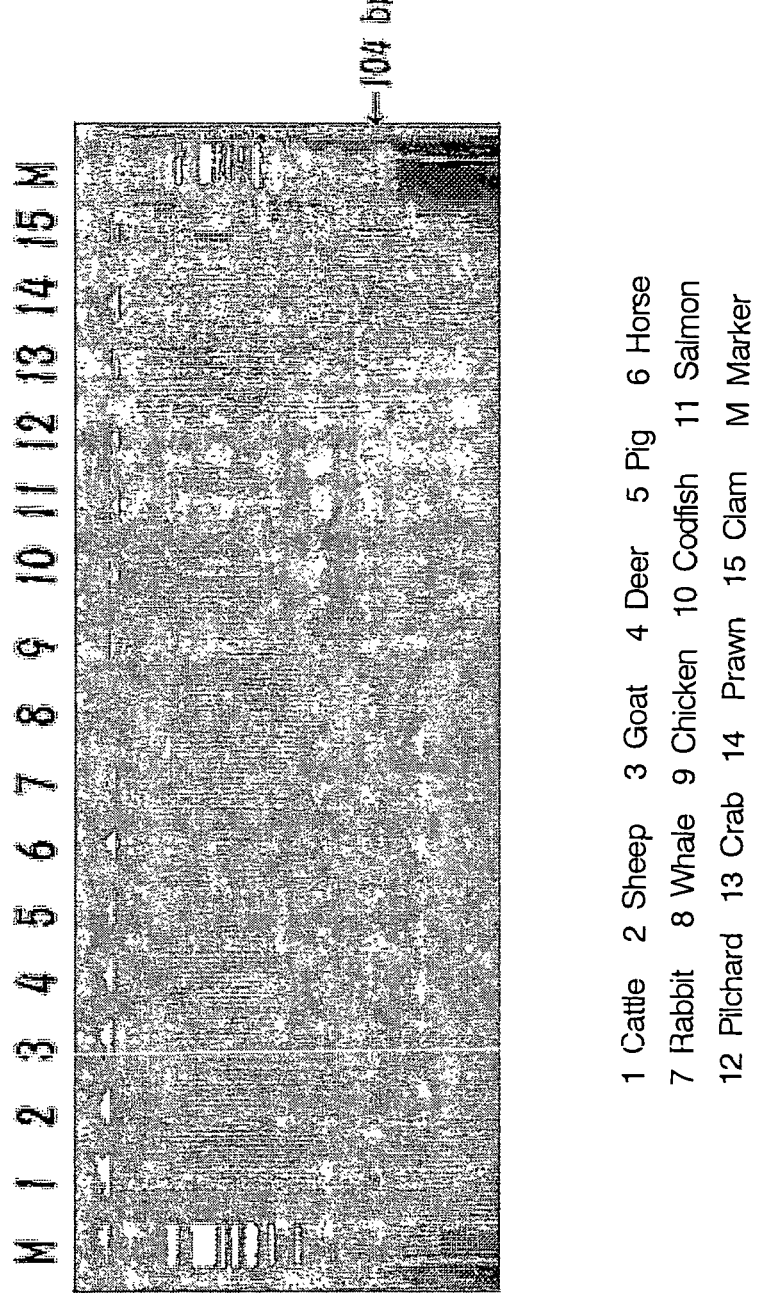
FIG. 7 is a photograph showing the results of electrophoresis after performing PCR using a primer pair (Fpr-F and Fpr-R) for detecting ruminant-specific DNA sequences and with DNAs derived from various types of animals serving as templates.

As shown in FIG. 7, by performing PCR using Fpr-F [SEQ ID NO: 5] and Fpr-R [SEQ ID NO: 6] as primers with each animal-derived DNA serving as a template, PCR products from DNAs derived from cattle, sheep, goat, and deer which are ruminants, were more clearly observed (104 bp band position). On the other hand, PCR products (DNA fragments) could not be detected in the DNA samples of animals that were not ruminants. That is, it was demonstrated that by using Fpr-F and Fpr-R as the primer pair, it is possible to more specifically detect only ruminant-derived DNA from various types of animal meat samples. Consequently, the combination of Fpr-F [SEQ ID NO: 5] and Fpr-R [SEQ ID NO: 6] is a primer pair that specifically detects DNAs derived from animal species of ruminant origin.

It should be noted that in Fpr-F [SEQ ID NO: 5] and Fpr-R [SEQ ID NO: 6], "r" is "g" or "a", and "k" is "g" or "t". That is, these are primer mixtures, but it should be apparent to those skilled in the art that each can be used independently.

Example 4

Specific Detection of Cattle-Derived DNA Sequence-1

Specific detection of a cattle-derived DNA sequence was performed using the various primer pairs listed in Table 1. PCR was performed under the same conditions as those of Example 1, except that DNAs prepared from cattle, sheep, goat, pig, and chicken meat were served as templates. The results are shown in FIGS. 8 to 10.

TABLE 1

Figure 8:
FIG. 8 is a photograph showing the results of electrophoresis after performing PCR using a primer pair (cow3 and cow51) for detecting cattle-specific DNA sequences and with DNAs derived from various types of animals serving as templates.
Figure 9:
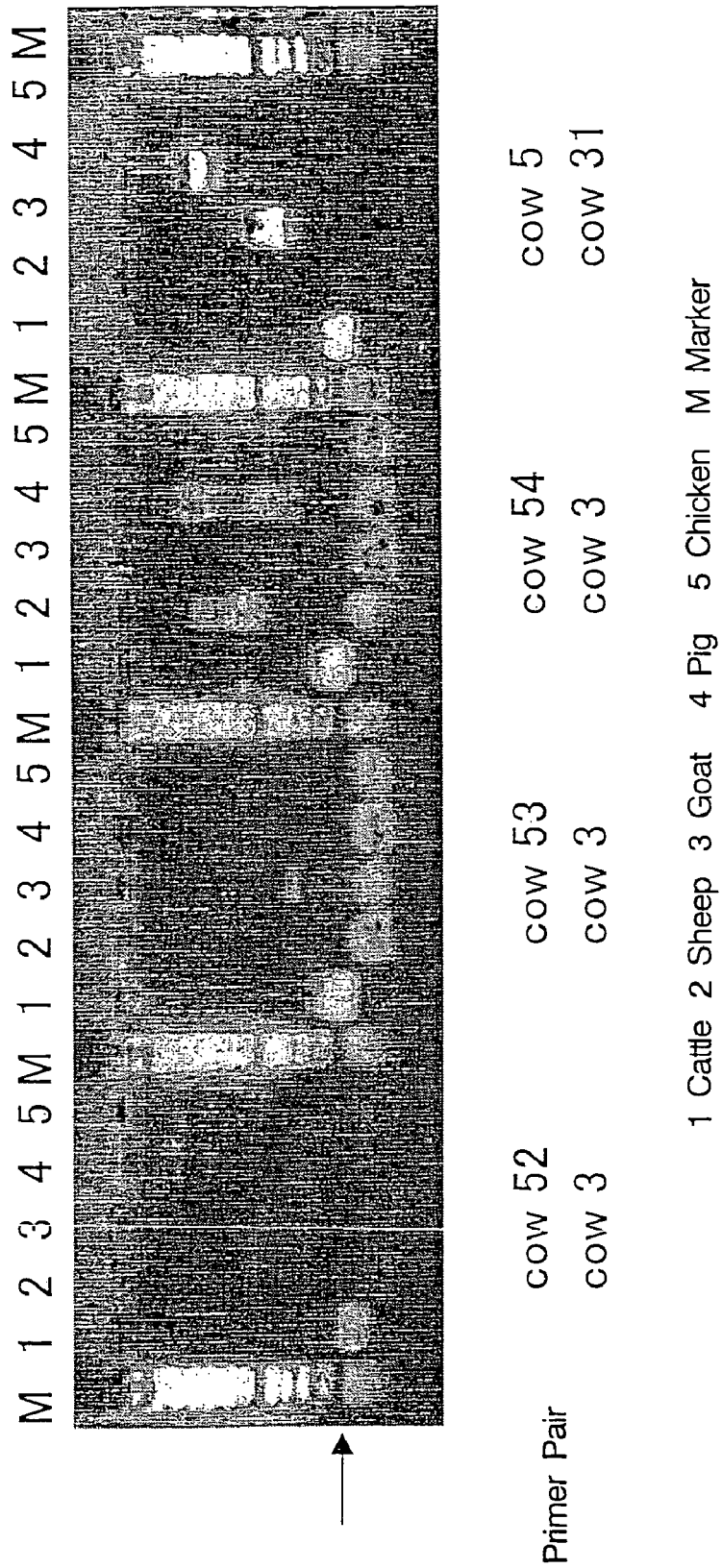
FIG. 9 is a photograph showing the results of electrophoresis after performing PCR using various primer pairs for detecting cattle-specific DNA sequences and with DNAs derived from various types of animals serving as templates.
Figure 10:
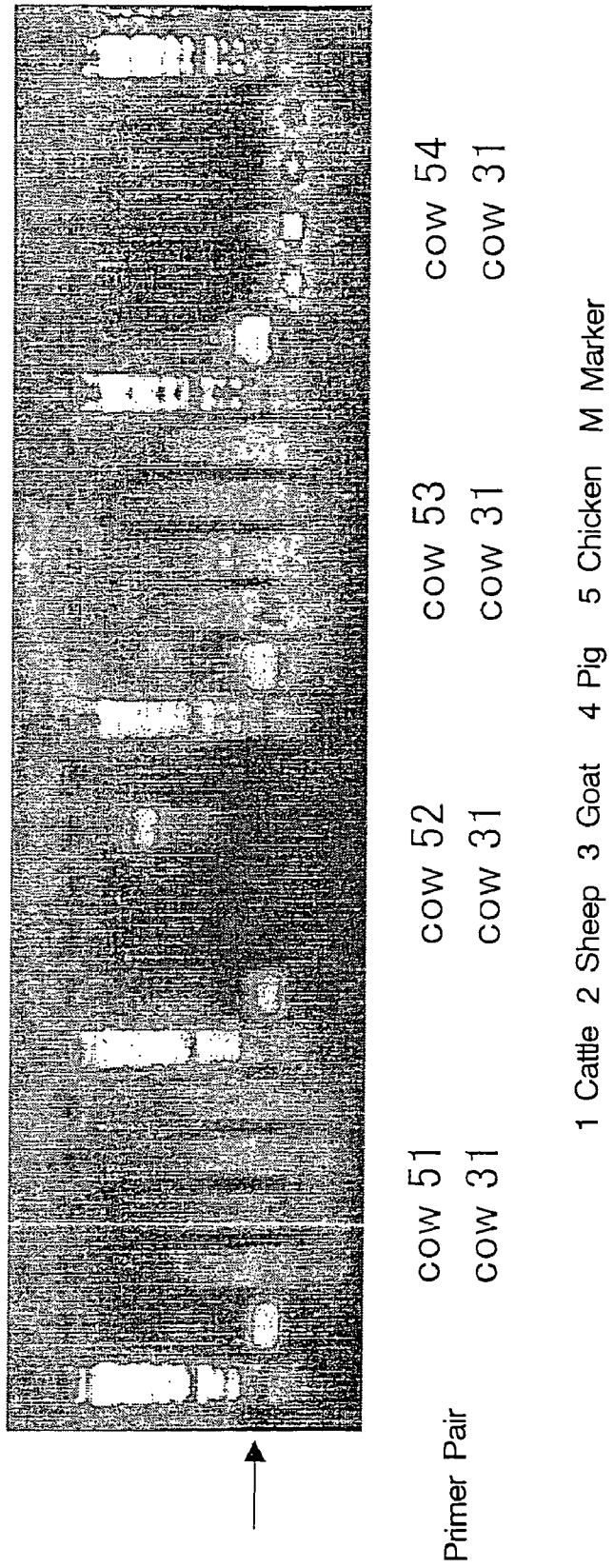
FIG. 10 is a photograph showing the results of electrophoresis after performing PCR using various primer pairs for detecting cattle-specific DNA sequences and with DNAs derived from various types of animals serving as templates.

| Primer | | Anealing | Result |
|---|---|---|---|
| 5' cow51 | SEQ ID NO: 8 | 55° C. 2 min | FIG. 8 |
| 3' cow3 | SEQ ID NO: 12 | | |
| 5' cow52 | SEQ ID NO: 9 | 52° C. 2 min | FIG. 9 |
| 3' cow3 | SEQ ID NO: 12 | | |
| 5' cow53 | SEQ ID NO: 10 | 52° C. 2 min | FIG. 9 |
| 3' cow3 | SEQ ID NO: 12 | | |
| 5' cow54 | SEQ ID NO: 11 | 52° C. 2 min | FIG. 9 |
| 3' cow3 | SEQ ID NO: 12 | | |
| 5' cow5 | SEQ ID NO: 7 | 52° C. 2 min | FIG. 9 |
| 3' cow31 | SEQ ID NO: 13 | | |
| 5' cow51 | SEQ ID NO: 8 | 56° C. 2 min | FIG. 10 |
| 3' cow31 | SEQ ID NO: 13 | | |
| 5' cow52 | SEQ ID NO: 9 | 52° C. 2 min | FIG. 10 |
| 3' cow31 | SEQ ID NO: 13 | | |
| 5' cow53 | SEQ ID NO: 10 | 56° C. 2 min | FIG. 10 |
| 3' cow31 | SEQ ID NO: 13 | | |
| 5' cow54 | SEQ ID NO: 11 | 56° C. 2 min | FIG. 10 |
| 3' cow31 | SEQ ID NO: 13 | | |
| 5' cow5 | SEQ ID NO: 7 | 46° C. 2 min | not shown |
| 3' cow3 | SEQ ID NO: 12 | | |

The results shown in FIG. 8 indicate that if cow51 [SEQ ID NO: 8] and cow3 [SEQ ID NO: 12] are used as the primer pair, then DNA fragments the same size as the PCR product (DNA fragments) obtained from cattle-derived meat did not find when sheep, goat, pig, or chicken DNA served as templates. It is clear that the combination of cow52 and cow3 of FIG. 9 and the combination of cow52 and cow31 of FIG. 10 are particularly suitable primer pairs for cattle-specific DNA detection, because similar DNA fragments were not detected in the samples of other animal species. On the other hand, as shown in FIG. 9, when cow5 [SEQ ID NO: 7] and cow31 [SEQ ID NO: 13] are used as the primer pair, a band of the same size as the DNA fragment obtained using a cattle DNA as a template was slightly found in sheep. Likewise, in FIG. 10, when the primer pair cow51 [SEQ ID NO: 8] and cow31 [SEQ ID NO: 13], and the primer pair cow53 [SEQ ID NO: 10] and cow31 [SEQ ID NO: 13] are used, a band the same size as the DNA fragment obtained using cattle DNA as a template was observed.

Example 5

Specific Detection of Cattle-Derived DNA Sequence-2

With the 15 types of DNA samples prepared in the same manner as in Example 1 serving as templates, PCR was performed using Fpc-F [SEQ ID NO: 14] and Fpc-R [SEQ ID NO: 15] as the 5' primer and the 3' primer, respectively. The PCR conditions were as follows: heat denaturing at 95° C. for 9 minutes, followed by the cycle of reactions of denaturing at 92° C. for 30 seconds, annealing at 55° C. for 30 seconds, and extending at 72° C. for 30 seconds repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. The results are shown in FIG. 11.

Figure 11:
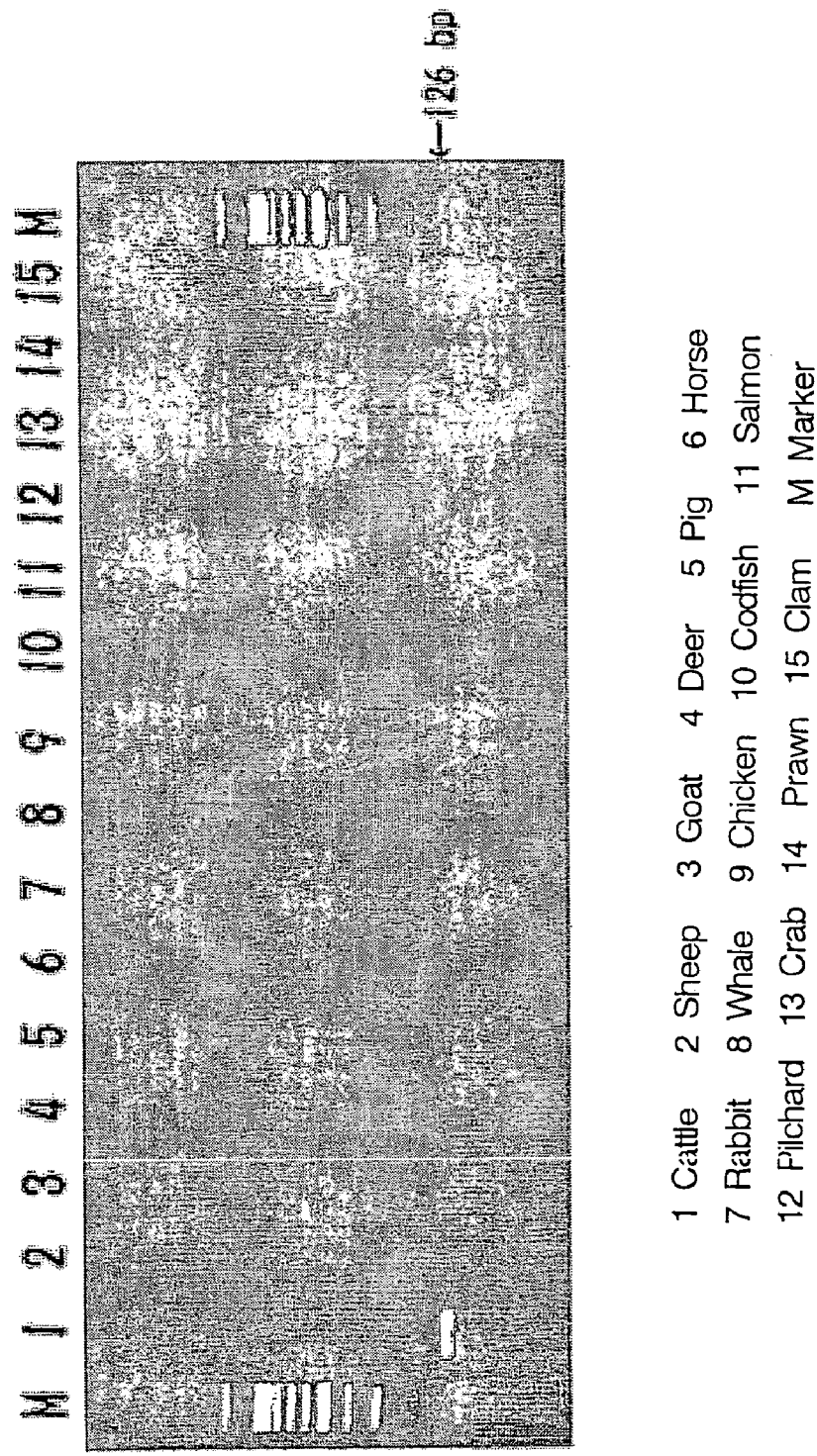
FIG. 11 is a photograph showing the results of electrophoresis after performing PCR using a primer pair (Fpc-F and Fpc-R) for detecting cattle-specific DNA sequences and with DNAs derived from various types of animals serving as templates.

As shown in FIG. 11, by performing PCR using Fpc-F [SEQ ID NO: 14] and Fpc-R [SEQ ID NO: 15] as primers with each animal-derived DNA serving as a template, the PCR product from only cattle-derived DNA was detected (126 bp band position). That is, it was demonstrated that by using Fpc-F and Fpc-R as the primer pair, it is possible to detect with extreme specificity only cattle-derived DNA from various types of animal meat samples. Consequently, the combination of Fpc-F [SEQ ID NO: 14] and Fpc-R [SEQ ID NO: 15] is a primer pair that specifically detects DNAs derived from animal species of bovine origin.

Example 6

Specific Detection of Pig-Derived DNA Sequence-1

Specific detection of a pig-derived DNA sequence was performed using the various primer pairs listed in Table 2. PCR was performed under the same conditions as those of Example 1, except that DNAs prepared from cattle, sheep, goat, pig, and chicken meat were served as templates.

TABLE 2

Figure 12:
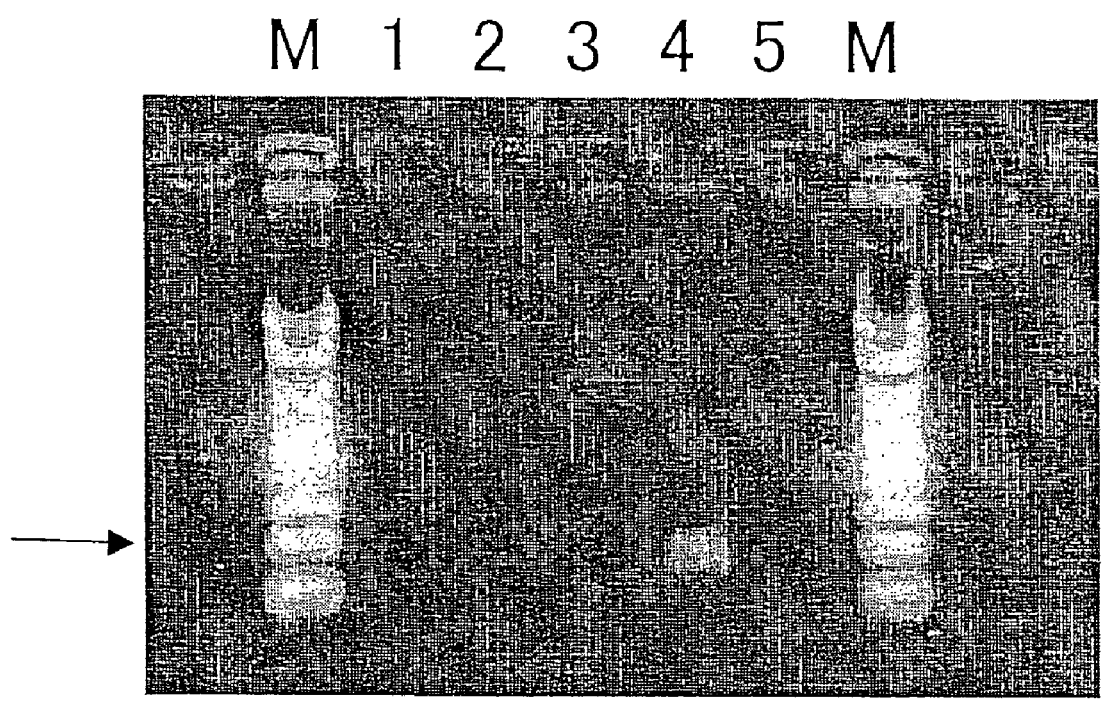
FIG. 12 is a photograph showing the results of electrophoresis after performing PCR using a primer pair (pig51 and pig3) for detecting pig-specific DNA sequences and with DNAs derived from various types of animals serving as templates.

| | Primer | Anealing | Result |
|---|---|---|---|
| 5' pig5 | SEQ ID NO: 16 | 46° C. 2 min | not shown |
| 3' pig3 | SEQ ID NO: 19 | | |
| 5' pig51 | SEQ ID NO: 17 | 58° C. 2 min | FIG. 12 |
| 3' pig3 | SEQ ID NO: 19 | | |
| 5' pig5 | SEQ ID NO: 16 | 46° C. 2 min | not shown |
| 3' pig31 | SEQ ID NO: 20 | | |
| 5' pig5 | SEQ ID NO: 16 | 46° C. 2 min | not shown |
| 3' pig32 | SEQ ID NO: 21 | | |

TABLE 2-continued

| | Primer | Anealing | Result |
|---|---|---|---|
| 5' pig51 | SEQ ID NO: 17 | 55° C. 2 min | not shown |
| 3' pig31 | SEQ ID NO: 20 | | |
| 5' pig51 | SEQ ID NO: 17 | 55° C. 2 min | not shown |
| 3' pig32 | SEQ ID NO: 21 | | |

FIG. 12 shows the results obtained by using pig51 [SEQ ID NO: 17] and pig3 [SEQ ID NO: 19] as the primer pair. As is clear from FIG. 12, PCR products (DNA fragments) were detected only in the sample derived from pig meat (band position indicated by the arrow). Consequently, this primer pair is useful for specifically detecting pig-derived DNA sequences.

Example 7

Specific Detection of Pig-Derived DNA Sequence-2

With the 15 types of DNA samples prepared in the same manner as in Example 1 serving as templates, PCR was performed using pig5-3 [SEQ ID NO: 18] and pig32-2 [SEQ ID NO: 22] as the 5' primer and the 3' primer, respectively. The PCR conditions were as follows: heat denaturing at 95° C. for 9 minutes, followed by the cycle of reactions of denaturing at 92° C. for 30 seconds, annealing at 60° C. for 1 minute, and extending at 72° C. for 1 minute repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. The results are shown in FIG. 13.

Figure 13:
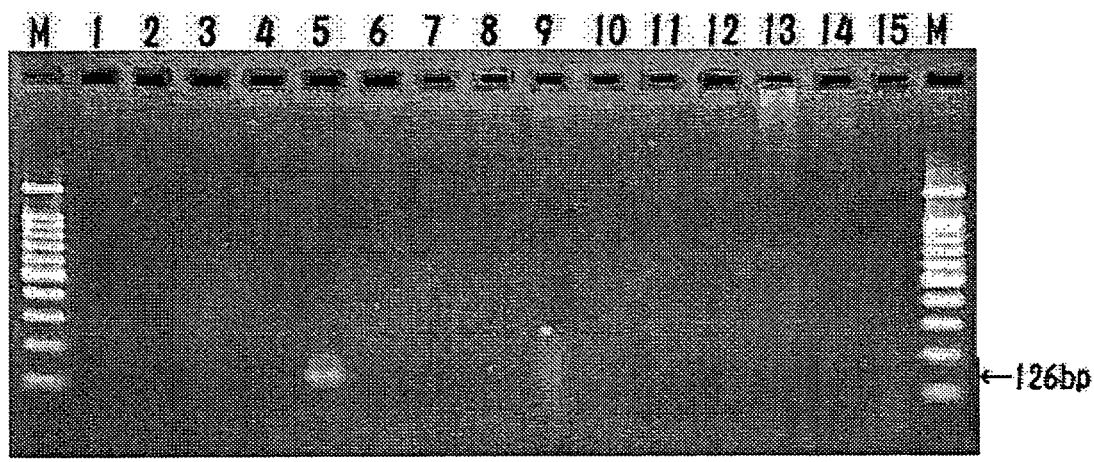
FIG. 13 is a photograph showing the results of electrophoresis after performing PCR using a primer pair (pig5-3 and pig32-2) for detecting pig-specific DNA sequences and with DNAs derived from various types of animals serving as templates.

As shown in FIG. 13, by performing PCR using pig5-3 [SEQ ID NO: 18] and pig32-2 [SEQ ID NO: 22] as primers with each animal-derived DNA serving as a template, the PCR product from only DNA derived from pig was observed (band position indicated by the arrow). On the other hand, PCR products could not be detected in the DNA samples of other animals. That is, it was demonstrated that by using pig5-3 and pig32-2 as the primer pair, it is possible to detect with only pig-derived DNA among various types of animal meat samples. Consequently, the combination of pig5-3 [SEQ ID NO: 18] and pig32-2 [SEQ ID NO: 22] is a primer pair that very specifically detects DNAs derived from animal species of pig origin.

Example 8

Specific Detection of Sheep-Derived DNA Sequence

Figure 14:
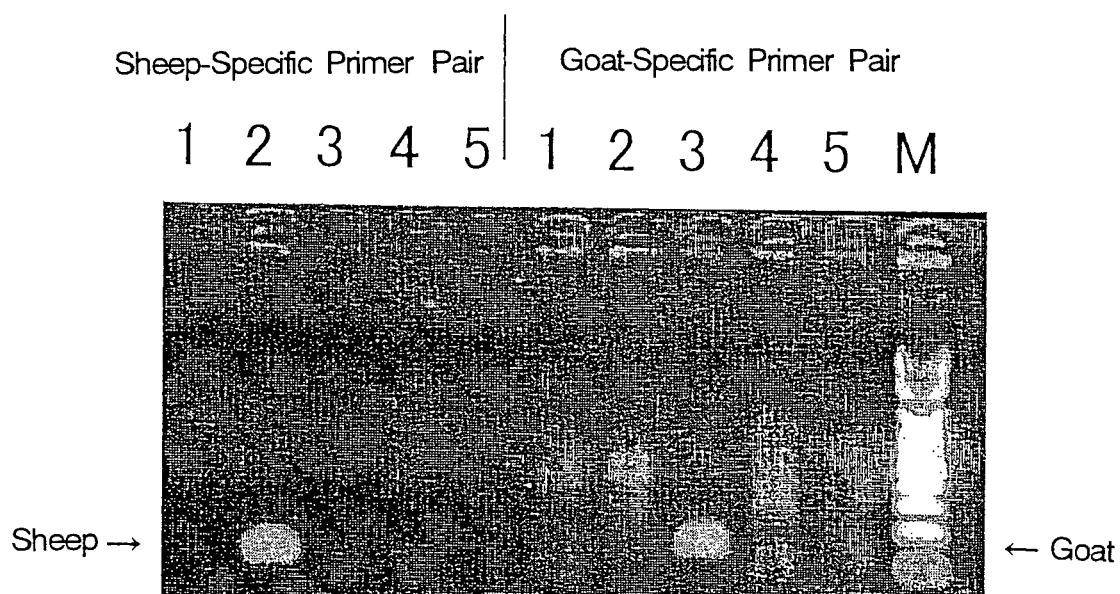
FIG. 14 is a photograph showing the results of electrophoresis after performing PCR using a primer pair (sheep5 and sheep3) for detecting sheep-specific DNA sequences and a primer pair (goat5 and goat3) for detecting goat-specific DNA sequences, and with DNAs derived from various types of animals serving as templates.

Specific detection of a sheep-derived DNA sequence was performed using sheep5 [SEQ ID NO: 23] and sheep3 [SEQ ID NO: 24] as the 5' primer and the 3' primer, respectively. PCR was performed under the same conditions as those of Example 1, except that DNAs prepared from cattle, sheep, goat, pig, and chicken meat were served as templates and that the annealing conditions were set to two minutes at 46° C. The results are shown in FIG. 14.

These results demonstrate that specific detection of a sheep-derived DNA sequence is possible using sheep5 [SEQ ID NO: 23] and sheep3 [SEQ ID NO: 24] as the primer pair.

Example 9

Specific Detection of Goat-Derived DNA Sequence

Specific detection of a goat-derived DNA sequence was performed using goat5 [SEQ ID NO: 25] and goat3 [SEQ ID NO: 26] as the 5' primer and the 3' primer, respectively. PCR was performed under the same conditions as those of Example 1, except that DNAs prepared from cattle, sheep, goat, pig, and chicken meat were served as templates and that the annealing conditions were set to two minutes at 46° C. The results are shown in FIG. 14.

These results demonstrate that specific detection of a goat-derived DNA sequence is possible using goat5 [SEQ ID NO: 25] and goat3 [SEQ ID NO: 26] as the primer pair.

Example 10

Specific Detection of Chicken-Derived DNA Sequence

Specific detection of a chicken-derived DNA sequence was performed using the various primer pairs listed in Table 3 as the 5' and the 3' primers. PCR was performed under the same conditions as those of Example 1, except that DNAs prepared from cattle, sheep, goat, pig, and chicken meat were served as templates. The results obtained by using chick5 [SEQ ID NO: 28] and chick3 [SEQ ID NO: 30] as the primers are shown in FIG. 15.

TABLE 3

Figure 15:
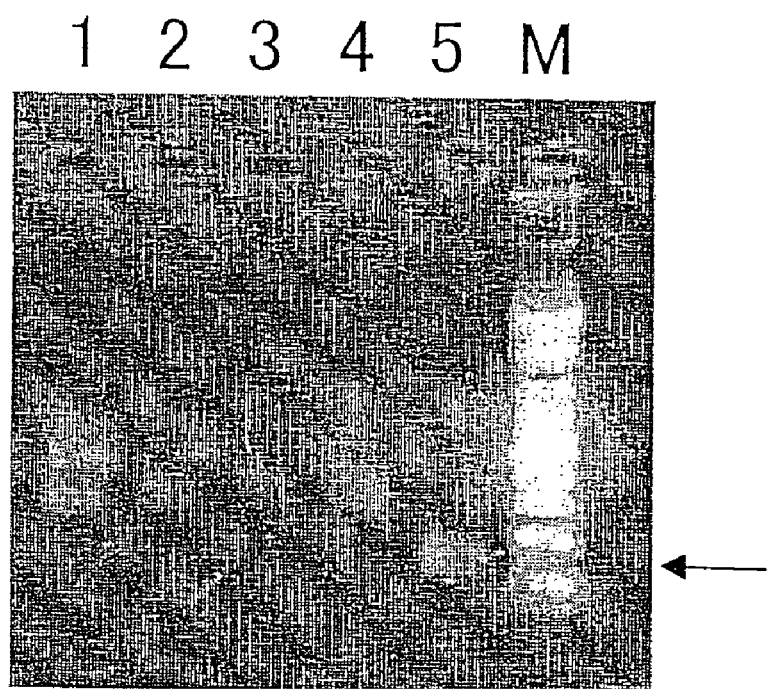
FIG. 15 is a photograph showing the results of electrophoresis after performing PCR using a primer pair for detecting chicken-specific DNA sequences and with DNAs derived from various types of animals serving as templates.

| Primer | | Anealing | Result |
|---|---|---|---|
| 5' chick5 | SEQ ID NO: 28 | 46° C. 2 min | FIG. 15 |
| 3' chick3 | SEQ ID NO: 30 | | |
| 5' chick51 | SEQ ID NO: 29 | 50° C. 2 min | not shown |
| 3' chick3 | SEQ ID NO: 30 | | |
| 5' chick5 | SEQ ID NO: 28 | 50° C. 2 min | not shown |
| 3' chick31 | SEQ ID NO: 31 | | |
| 5' chick51 | SEQ ID NO: 29 | 60° C. 2 min | not shown |
| 3' chick31 | SEQ ID NO: 31 | | |

As shown in FIG. 15, specific detection of a chicken-derived DNA sequence is possible using chick5 [SEQ ID NO: 28] and chick3 [SEQ ID NO: 30] as the primer pair (band position indicated by the arrow).

Example 11

Detection of Cattle-Derived Component in Mixed Feed-1

Figure 16:
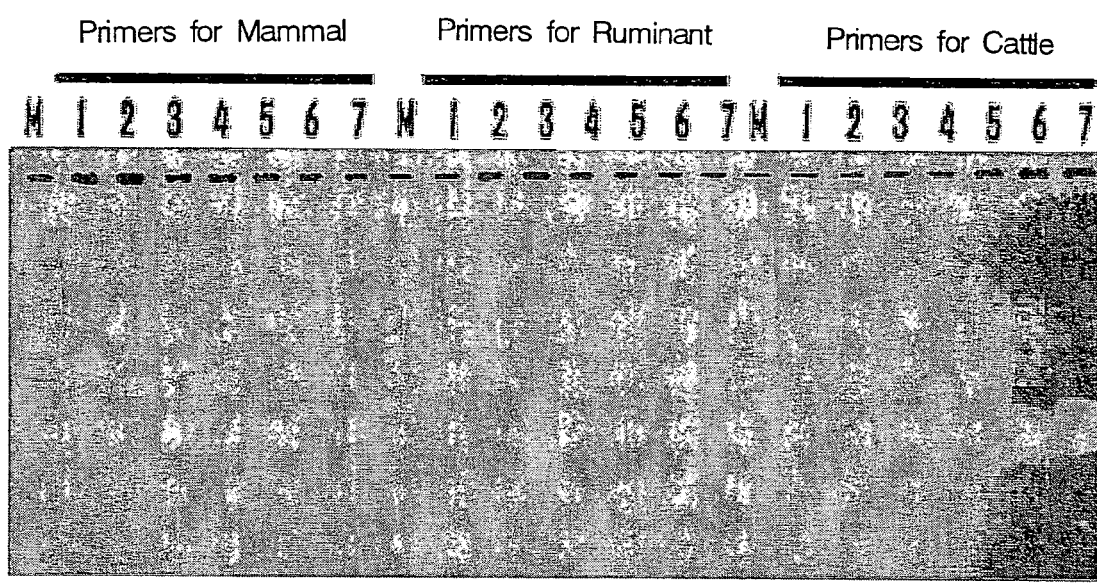
FIG. 16 is an electrophoresis photograph showing the results of the detection of DNA, using mammal-specific primer pairs, using various primer pairs, in mixed feed for livestock that contains cattle meat and bonemeal.

Meat and bonemeal derived from cattle (Australian bred) was mixed into mixed feed for livestock (main components: corn, milo, gluten feed, bran, rice bran, soy oil cake, rapeseed oil cake) at a predetermined ratio. Then, as in Example 1, 100 mg of the feed obtained was suspended in ten times that amount of buffer solution, and ground by a bead grinding method. Then, DNA was extracted using a commercially available tissue cell mitochondrial DNA extraction kit (manufactured by Wako Pure Chemical Industries, Ltd., Japan). Using this DNA as a template, PCR was performed under the same conditions as in Example 1 using anicon5 [SEQ ID NO: 1] and anicon3 [SEQ ID NO: 2], which are the primer pair for specifically detecting mammalian-derived DNA sequences used in Example 1, Fpr-F [SEQ ID NO: 5] and Fpr-R [SEQ ID NO: 6], which are the primer pair for specifically detecting ruminant-derived DNA sequences used in Example 3, and Fpc-F [SEQ ID NO: 14] and Fpc-R [SEQ ID NO: 15], which are the primer pair for specifically detecting cattle-derived DNA sequences used in Example 5. The results are shown in FIG. 16. In all cases where these primer pairs were used, it was possible to detect cattle meat and bonemeal contained in the feed at 0.01 wt %.

Example 12

Detection of Cattle-Derived Component in Mixed Feed-2

Figure 17:
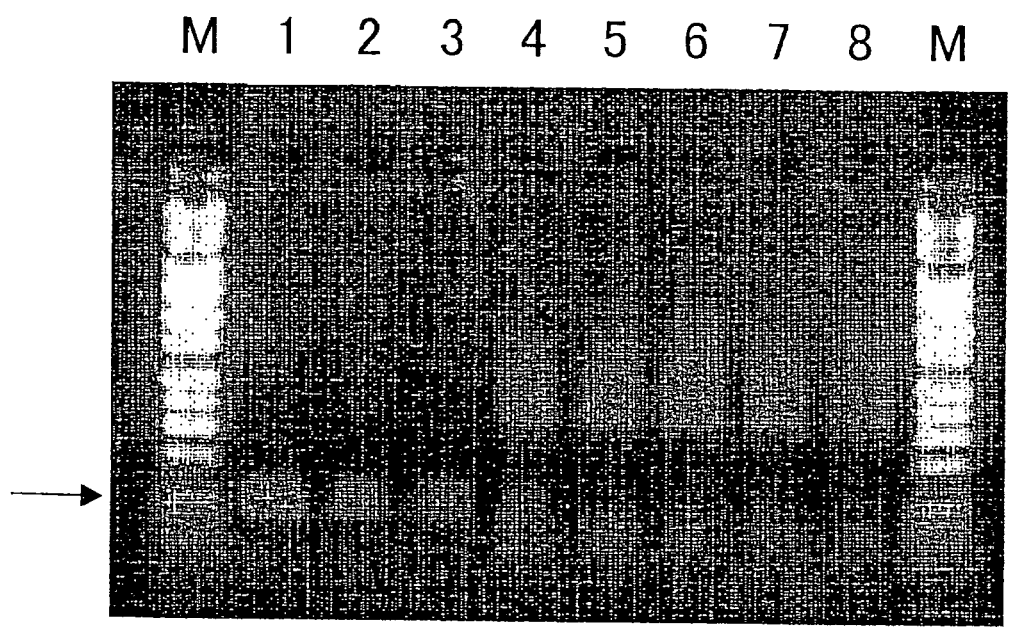
FIG. 17 is an electrophoresis photograph showing the results of the detection of DNA, using ruminant-specific primer pairs, in mixed feed for livestock that includes cattle meat and bonemeal.

PCR was performed under the same conditions as in Example 2, except that DNA extracted from mixed feed in the same manner as in Example 11 was served as a template and that the primer pair rumicon5 [SEQ ID NO: 3] and rumicon3 [SEQ ID NO: 4] for specifically detecting ruminant-derived DNA sequences that is used in Example 2 was used. The results are shown in FIG. 17. Detection was possible even in a case where the feed contained 0.1 to 1 wt % meat and bonemeal.

Example 13

Detection of Cattle-Derived Component in Mixed Feed-3

Figure 18:
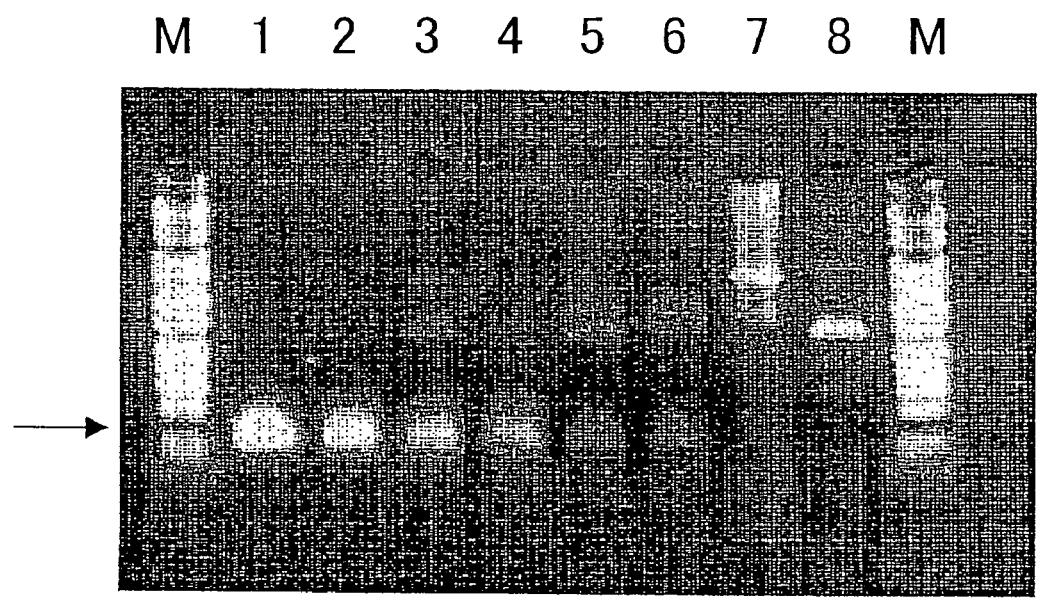
FIG. 18 is an electrophoresis photograph showing the results of the detection of DNA, using cattle-specific primer pairs, in mixed feed for livestock that contains cattle meat and bonemeal.

PCR was performed under the same conditions as in Example 3, except that DNA extracted from mixed feed in the same manner as in Example 11 was served as a template and that the cattlederived DNA-specific primer pair of cow52 [SEQ ID NO: 9] and cow31 [SEQ ID NO: 13] that was used in Example 3 was used. The results are shown in FIG. 18. Detection was possible even in a case where meat and bonemeal was only contained in the feed at a mere 0.001 wt %.

Example 14

Specific Detection of Fish-Derived DNA Sequence

Fishmeal is often a mixture of various types of fish. Thus, several primer regions were selected based on the alignment of the DNA sequences of the atp8 gene and proximal regions shown in FIG. 3 in order to detect a wide range of components derived from various types of fish. The underlined portion in FIG. 3 is the atp8 gene of a pilchard, and the asterisk bellowing the alignment indicates the portion where bases are conserved among the DNA sequences.

A commercially available tissue cell mitochondrial DNA extraction kit (manufactured by Wako Pure Chemical Industries, Ltd., Japan) was used in the same manner as in Example 1 to prepare DNA from the 26 types of plants and animals shown in Table 4 below. PCR was carried out using this DNA solution as a template and using the various combinations of 5' and 3' primers selected based on the sequence alignment of FIG. 3. As for the primers used, the 5' side primers used were fish5 [SEQ ID NO: 32], fish51 [SEQ ID NO: 34], fish5-1 [SEQ ID NO: 38], and fish5-2 [SEQ ID NO: 39], and the 3' side primers used were fish3-1 [SEQ ID NO: 33], fish3 [SEQ ID NO: 35], fish31 [SEQ ID NO: 36], fish31-1 [SEQ ID NO: 37], fish3-2 [SEQ ID NO: 40], and fish3-3 [SEQ ID NO: 41]. The PCR conditions were as follows: reaction buffer solution (10 mM Tris-HCl, pH 8.3, 50 mM KCl, 1.5 mM $MgCl_2$, 0.001% (w/v) gelatin); heat denaturing at 95° C. for 9 minutes, followed by the cycle of reactions of denaturing at 92° C. for 30 seconds, annealing at 55° C. for 30 seconds, and extending at 72° C. for 30 seconds repeated 45 times, and lastly, the product was allowed to react at 72° C. for five minutes. After PCR, the reaction mixture was subjected to agarose gel electrophoresis, and the PCR product (DNA fragments) was detected by ethidium bromide staining. In the positive control, PCR was performed with a solution of sardine-derived DNA obtained in the same manner as in Example 1 from crushed sardine meat serving as the template.

In the negative control, PCR was performed with a blank in which the template DNA was not added to the PCR reaction mixture.

Table 4 shows the results obtained with the combination of fish5 [SEQ ID NO: 32] and fish3-1 [SEQ ID NO: 33]. It should be noted that in the assessment column of Table 4, the cases where a band was not detected in the negative control, but a band of a target size was detected in the positive control, and a band of the same size as that detected in the positive control was detected in the sample, were regarded as positive.

TABLE 4

| Animal | Assesment* | Animal | Assesment* |
|---|---|---|---|
| Cattle(Beef cattle) | − | Human | − |
| Cattle(Holstein) | − | Scad | − |
| Cattle(Japanese black) | − | Sardine | + |
| Cattle(Red hair) | − | Flatfish | ± |
| Cattle(F2) | − | Salmon | + |
| Sheep | − | Alaska pollack | + |
| Goat | − | Tuna | + |
| Deer | − | Crab | − |
| Pig | − | Lady crab | + |
| Horse | − | Prawn | − |
| Rabbit | − | Squid | − |
| Whale | − | Clam | − |
| Chicken | − | Corn | − |

*+; Detection of band at 284 bp, ±; Detection of unclear band at 284 bp, −; Under detection limit of band at 284 bp
Detection was performed with agarose gel electrophoresis and ethidium bromide staining.

As shown in the assessment column of Table 4, a band was detected at the position of 284 bp in DNA samples taken from sardine, flatfish, salmon, Alaska Pollack, tuna, and lady crab. On the other hand, a band was under detectable in mammalian, chicken, and corn DNA samples. Consequently, it is clear that the primer pair of fish5 [SEQ ID NO: 32] and fish3-1 [SEQ ID NO: 33] allows the major fish types often used to produce fishmeal to be detected.

Apart from this, about 100 kinds of fishmeal was examined by extracting DNA in the same manner as above. The results showed that a band can be detected at the position of interest in about 90 percent of the fishmeal. These results also indicated that wide ranging detection is possible for DNA derived from various types of fishes.

Example 15

Fish-Derived DNA Sequence Addition Testing and Detection Limit

Whether or not it is possible to detect fishmeal mixed into commercially available mixed feed for raising cattle or chickenmeal was examined. The raw material of the fishmeal was mackerel and saury, and the fishmeal used was passed through a 0.5 mm mesh wire sieve. As regards the mixed feed, commercially available mixed feed for cattle was crushed with a crusher and a triturator, and was passed through a 0.5 mm mesh wire sieve. It should be noted that the mixture proportions of the mixed feed are as shown below in Table 5. The chickenmeal was commercially available chickenmeal, and had been passed through a 0.5 mm mesh wire sieve.

TABLE 5

| Feed | Type of material | Ratio(%) | Raw materials |
|---|---|---|---|
| Mixed feed for raising dairy cattle | Chaff and bran | 37 | Corn gluten feed, Rice bran, Bran, Soybean hull |
|  | Cereals | 36 | Corn, Rye, Wheat flour, Milo |
|  | Vegetable oil cake | 19 | Rapeseed oil cake, Soy oil cake |
|  | Others | 8 | Syrup, Calcium carbonate, Salt |
| Mixed feed for raising beef cattle | Cereals | 66 | Corn, Barley, Wheat |
|  | Chaff and bran | 28 | Bran, Corn gluten feed |
|  | Vegetable oil cake | 4 | Soy oil cake |
|  | Others | 2 | Alfalfa meal |

Samples containing 1 wt % fishmeal in the above mixed feed and chickenmeal were prepared. As regards these samples and the samples without fishmeal, DNAs were extracted as in Example 1, and PCR was performed using the primer pair of fish5 [SEQ ID NO: 32] and fish3-1 [SEQ ID NO: 33].

Fish-derived DNA was detected in the mixed feed and chickenmeal containing 1 wt % fishmeal. On the other hand, DNA was not detected from the samples to which fishmeal was not added. Consequently, it was clear that the fishmeal used in this example can be detected even when contained at 1 wt %.

Next, the detection limit of fishmeal contaminated in mixed feed was examined. Fishmeal was added at 10, 1, 0.1, and 0.01 wt % to the mixed feed for raising dairy cattle of Table 5, and using the same procedure as that of Example 14, DNA was extracted in duplicate for each sample, and for each extracted sample PCR was performed in duplicate. When both of the two DNA extracts resulted in positive, an assessment of positive was reached. The detection limit for the fishmeal when using the primer pair of fish5 [SEQ ID NO: 32] and fish3-1 [SEQ ID NO: 33] was about 1 wt %.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A primer pair for detection of DNAs derived from animals belonging to ruminants, the primer pair being a combination of a first primer consisting of the DNA sequence of SEQ ID NO: 3 and a second primer consisting of the DNA sequence of SEQ ID NO: 4, or a combination of a first primer consisting of the DNA sequence of SEQ ID NO: 5 and a second primer consisting of the DNA sequence of SEQ ID NO: 6, wherein the primer pair does not detect or prime a non-ruminant DNA and does detect or prime ruminant-derived DNA.

2. The primer pair of claim 1, the ruminant is selected from the group consisting of cattle, sheep, goat, and deer.

3. A kit for detecting an animal-derived component present in a sample comprising: a primer pair, the primer pair being a combination of a first primer consisting of the DNA sequence of SEQ ID NO: 3 and a second primer consisting of the DNA sequence of SEQ ID NO: 4, or a combination of a first primer consisting of the DNA sequence of SEQ ID No: 5 and a second primer consisting of the DNA sequence of SEQ ID NO: 6, wherein the primer pair does not detect or prime a non-ruminant DNA and does detect or prime ruminant-derived DNA.

* * * * *